United States Patent [19]

Sher

[11] Patent Number: 5,697,459
[45] Date of Patent: Dec. 16, 1997

[54] DIRECTIONAL SELF-PROPELLED DRILL

[76] Inventor: Arieh Sher, 35 Spinoza, 76452 Rehovot, Israel

[21] Appl. No.: 671,048

[22] Filed: Jun. 25, 1996

Related U.S. Application Data

[63] Continuation-in-part of Ser. No. 473,880, Jun. 7, 1995, Pat. No. 5,592,866, which is a continuation of Ser. No. 100,949, Aug. 3, 1993, Pat. No. 5,467,684, which is a continuation-in-part of Ser. No. 83,760, Jun. 30, 1993, Pat. No. 5,350,390, which is a continuation of Ser. No. 857,556, Mar. 25, 1992, abandoned.

[51] Int. Cl.⁶ .................................................. E21B 4/02
[52] U.S. Cl. .................................................. 175/95; 175/106
[58] Field of Search .................................. 175/215, 320, 175/293, 323, 405, 94, 95, 106; 173/14, 53, 54, 55

[56] References Cited

U.S. PATENT DOCUMENTS

| | | | |
|---|---|---|---|
| 3,792,741 | 2/1974 | Hopler, Jr. | 175/11 |
| 4,126,193 | 11/1978 | Brown et al. | 175/171 |
| 4,314,615 | 2/1982 | Sodder, Jr. et al. | 175/94 |
| 4,359,109 | 11/1982 | Truong-Cao | 173/111 |
| 4,463,814 | 8/1984 | Horstmeyer et al. | 175/45 |
| 4,727,763 | 3/1988 | Georget | 74/129 |

*Primary Examiner*—Frank Tsay
*Attorney, Agent, or Firm*—Mark M. Friedman

[57] ABSTRACT

A self-propelled drill for drilling a bore or cleaning a pipe in straight and/or curved paths. The drill includes a piston having a working head which slides within a housing. A rotary piston driving mechanism featuring an endless groove converts longitudinal motion of the piston to a combined longitudinal and rotary movement of the working head. A housing gripping device fixes the drill to the wall of the bore to allow drilling while a working head gripping device fixes the working head to the walls of the bore to allow the drill to be periodically pulled forward.

16 Claims, 4 Drawing Sheets

DIRECTIONAL SELF-PROPELLED DRILL

This is a continuation-in-part of U.S. patent application Ser. No. 08/473,880, filed Jun. 7, 1995, now U.S. Pat. No. 5,592,866 which is a continuation of U.S. patent application Ser. No. 08/100,949 filed Aug. 3, 1993, now U.S. Pat. No. 5,467,684, which is a continuation-in-part of U.S. patent application Ser. No. 08/083,760, filed Jun. 30, 1993, now U.S. Pat. No. 5,350,390, which is a continuation of U.S. patent application Ser. No. 07/857,556, filed Mar. 25, 1992, now abandoned.

FIELD AND BACKGROUND OF THE INVENTION

The present invention relates to the field of drills, and more particularly to directional self-propelled earth boring drills, or pipe cleaner drills.

A rotary piston driving mechanism is described in U.S. Pat. No. 5,467,684 to Sher which is incorporated by reference in its entirety for all purposes as if fully set forth herein. In this patent a mechanism is described in which a longitudinal reciprocating motion of a piston in a cylinder is transformed to a combined rotary and longitudinal motion of the working head. The mechanism utilizes a closed wave-shaped groove defined in either the cylinder or the piston. Complementary guiding members project into the groove. When the piston is forced to move longitudinally, the groove slides over the guiding members to cause rotation.

The main requirements of an earth drill are the rotation of the working head and the ability to remove debris.

Earth drills are known. Direct drive of a working head has been suggested. Also suggested has been the use of downhole motors which can be classified as turbodrills, electric drills, positive displacement motors, and the like. The debris is usually removed by fluid jets.

Other requirements of earth drills are the ability to directionally drill and the ability to be self-propelling.

Directional drilling enables drilling in curved paths. An example is disclosed in U.S. Pat. No. 4,522,272 to Beimgraben. A self-propelled drill is a drill which is capable of advancing in the bore without an external force being imposed on it, see, for example U.S. Pat. No. 4,314,615 to Sodder et al.

The present invention can also be used as a pipe cleaner or as a drain cleaner. Apart from apparatus which suggest cleaning of pipe by water jets, a common apparatus is the one that uses a flexible shaft. The advantage of the flexible shaft lies in the fact that it is capable of advancing through curved paths. However, the moment that can be transferred to the working head is limited.

It is to be understood that this invention can also be used in other areas, such as in surgical operation, and the like.

SUMMARY OF THE INVENTION

It is an object of the present invention to provide a method and an apparatus for drilling purposes, specifically earth drills and pipe cleaners or drain cleaners.

It is another object of the present invention to provide a drill which is self-propelled.

Still another object of the present invention is to provide a directional drill that can be directed along curved paths.

A further object of the present invention is to provide a drill that has a lumen for removing the debris by fluid jet.

It is also an object of the present invention to provide a drill that has a lumen for inserting special accessories such as guide wire or optical fiber.

It is another object of the present invention to provide a system which includes a driving unit that can operate and automatically control the drill.

In accordance with a preferred embodiment of the present invention there is provided a drill which utilizes the rotary piston driving mechanism. This mechanism enables movement of a working head in a combined longitudinal and rotational motion. The drill is attached to a power unit via a bundle of flexible tubing surrounded by a jacket or alternatively, via a multilumen tubing, that is, a tubing which contains multiple lumens. Each lumen serves a specific function. In the driving unit, each lumen is connected to a pressure generator. In the preferred embodiment, the pressure generator is an electrical linear actuator. An electronic controller controls the sequence of operations of the linear actuators and the pressure in the lumen and/or the axial movement of the actuator. The piston of the drill is a double acting piston, which has two chambers, one serves for forward motion of the working head and the other for its backward motion. Two lumens are used for the forward and backward movements of the piston. This linear movement of the piston is transformed to the combined longitudinal and rotary motion of the working head.

Three or more lumens serve for gripping and directing the drill. These three or more lumens are connected to three or more balloons which are arranged circumferentially on the envelope of the drill at equal spacing. When the balloons are inflated they are pushed against the walls of the bore or the pipe wall. Once the drill is gripped in place, the working head is able to exert a torsional moment and an axial force without transferring these moments to the multilumen. Apart from gripping capability, these balloons also enable directional movement of the drill. When the balloons are equally pressurized the drill moves in a straight line. In cases in which the balloons are pressurized to unequal extents the drill is forced to change its direction.

An electronic sensor mounted on the drill measures the azimuth and the inclination angles of the drill. The data are sent to an electronic controller via electric wires that pass in a separate lumen of the multilumen. The controller adjusts the pressure in the balloons so that the drill follows a desired path. The controller supervises all the other phases of operation, as well.

During the drilling phase the number of revolutions of the working head is controlled by the controller and is a function of the hardness of the removed material. Independently of the number of revolutions performed by the working head, the last stroke should be such that the working head is pushed to its maximum forward position.

At the conclusion of the drilling phase, the gripping/directing balloons on the drill housing are deflated, whereas the balloon mounted on the working head is inflated, thereby gripping the working head. Then, the chamber that during the drilling phase causes the working head to move backwards is pressurized and the drill including the multilumen tube is pulled forward. The endless groove has a special design in which the segments of the groove are not equal. One segment is inclined, thus forcing the working head to rotate, while the adjacent segment is axially oriented. Thus, when the drill with the multilumen tube moves forward no torsional moment is exerted on the multilumen. This phase completes a cycle of motions and the procedure can be repeated over and over again.

An additional central lumen is reserved for fluid jets. The fluid removes the debris which is accumulated around the working head. When the drill is used for pipe cleaning, the debris is pushed forward in the pipe, whereas when the device is used as an earth drill the debris and the fluid moves backwards in the bore. This additional central lumen can also be used for other purposes such as for inserting an optical fiber. This may enable the plumber, for example, to see the type of obstruction in the pipe and to decide what type of working head should be used. This lumen can serve also for inserting a guide wire which may be used when the pipe is curved. In this case, the plumber first inserts the guide wire which is a flexible small diameter wire, and subsequently pushes the drill over the guide wire.

It should be noted here that the guide wire, the type of working head and the optical fiber are not part of the invention and therefore are not described in detail.

As used herein in the specification and claims, the terms 'drill' and 'drilling' are used generically to encompass drills and drilling operations of various type as well as various pipe cleaning and clearing operations.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
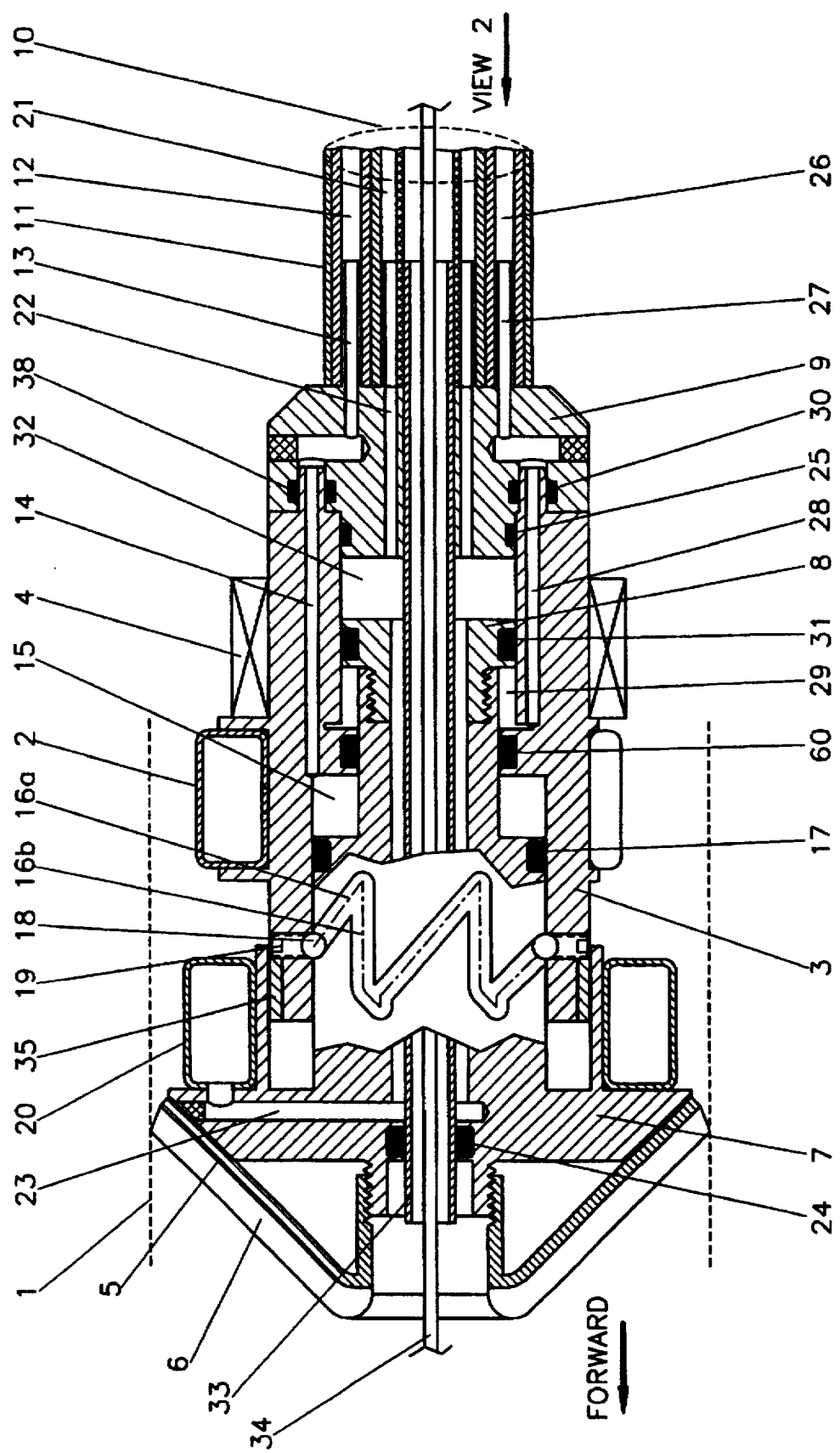
FIG. 1 is a view in longitudinal section of an illustrative embodiment of a directional self-propelled drill according to the present invention.
Figure 2:
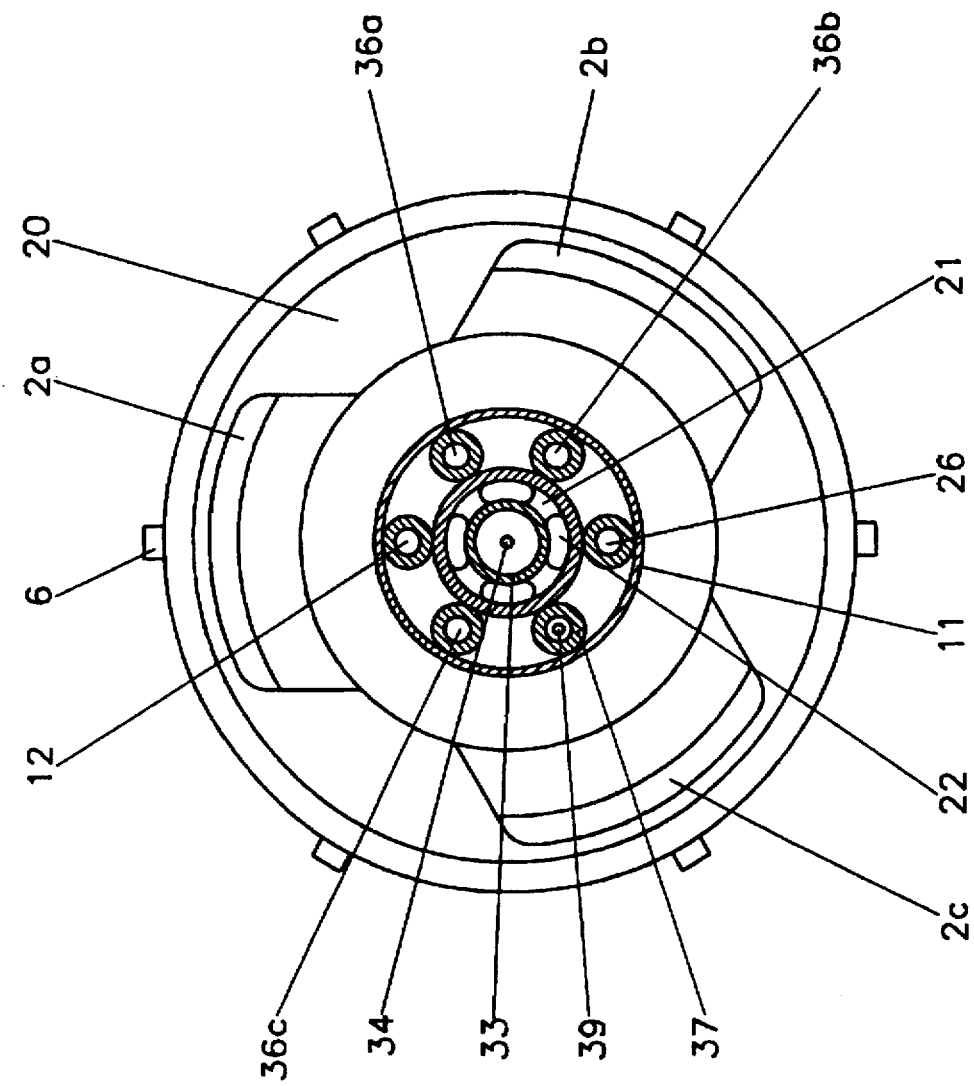
FIG. 2 is a view of the directional self-propelled drill of FIG. 1 along view 2 of FIG. 1.

An illustrative embodiment of a directional self-propelled drill according to the present invention is shown in FIGS. 1 and 2. The drilling procedure consists of four phases.

The first phase involves the gripping and directing of the drill. Gripping and directing the drill is effected by using the bore or pipe wall 1. Three cylinder gripping balloons 2a, 2b, 2c (FIG. 2, and collectively designated as '2' in FIG. 1) are located circumferentially on cylinder 3 at equal intervals or spacings. The arrangement of the three balloons 2a, 2b, 2c at 120° intervals is shown more clearly in FIG. 2. The three cylinder gripping balloons 2a, 2b, 2c are pressurized via lumens 36a, 36b, 36c, respectively (FIG. 2). When the three balloons 2a, 2b, 2c, are equally pressurized the longitudinal axis of the drill coincides with the axis of bore. When the three balloons 2a, 2b, 2c are not equally pressurized, the axes do not coincide which enables changing the direction of the drill.

The gripping of balloons 2a, 2b, 2c to wall 1 also enables the cutting action of the working head, as the drill in this situation can resist the torsional moment imposed by the working head. Positioning sensors 4 measure the azimuth and inclination angles of the drill and these data are transferred to a driving unit (as defined below) via electronic wire 39 located in lumen 37 (FIG. 2). This function of the driving unit, as well as other functions, are discussed below.

The second phase of the drilling process is the cutting phase. A working head 5 features cutting blades 6 is secured to piston 7. Piston 7 is located within cylinder 3. Ring 8 is fixedly assembled with piston 7. An adapter 9 is used to connect between cylinder 3 and a bundle of tubing 10 that are assembled together in a jacket 11. Alternatively, bundle 10 can be replaced by a multilumen which is a tube that contains multiple lumens. For convenience, both bundle of tubing and multilumen, as well as any other equivalent structure, will be referred to herein in the specification and claims as 'bundle' and will be designated by the numeral '10'.

Fluid pressure which is applied to lumen 12 is transferred to chamber 15 via channels 13 and 14. Sealing is achieved by O-rings 60, 17 and 38. The pressure forces piston 7 to move forward, but at the same time piston 7 is also forced to rotate. The rotation is achieved because one or more protrusions or balls 18 which are secured by set screws 19, ride in the inclined portion 16a of an endless groove. A more detailed description of the endless groove can be found in U.S. Pat. No. 5,467,684, which has been fully incorporated by reference for every purpose as if fully set forth herein.

In the third phase, the gripping action to wall 1 is changed from the cylinder gripping to the working head gripping. Working head gripping balloon 20 is pressurized until it is pressed against wall 1 so as to grip the working head. The pressure for gripping balloon 20 is transferred through lumen 21, passage 22 and channel 23. Sealing is achieved by O-rings 24, 25 and 31. The pressure in cylinder gripping balloon 2a, 2b, 2c is decreased so as to release the cylinder.

In the fourth phase, the drill advances in a forward direction. The rate of advance is exactly the stroke of the non-inclined endless groove segment 16b. This is effected by pressurizing lumen 26. The pressure is transferred to chamber 29 via channels 27 and 28. O-rings 60, 30 and 31 are used for sealing. As mentioned in the third phase, working head gripping balloon 20 is gripped to wall 1. The end result is that cylinder 3 together with bundle 10 are pulled forward. It should be noted that the endless groove segment 16b is substantially axially oriented in order to avoid torsional moment on bundle 10 as the drill is advanced forward. It is also noted that in order that chamber 29 is able to expand, the pressure in chamber 15 should be decreased, while the pressure in chamber 32 that is connected to working head gripping balloon 20 should be maintained. Controlling the pressures and other functions as well are effected by the driving unit in a way that is explained below. This phase completes one cycle and the procedure can be repeated over and over again.

The drill assembly further contains additional parts. A central tube 33 is secured to one end to adapter 9 and passes axially through the drill. Central tube 33 is used for supplying fluid jets to the working head in order to remove debris. Yet another usage of central tube 33 is to enable the insertion of special accessories, such as, for example, an optical fiber 34. Optical fiber 34 can be used for exploring the type of blockage in drain pipes, and to help the plumber decide the appropriate working head for doing the job. Another possible usage of central tube 33 is in curved pipes. First, a guide wire 34 is inserted through central tube 33 and subsequently, the drill is pushed over it with guide wire 34 serving to guide the insertion of the tool.

Bushing 35 reduces the bending moment exerted by working head 5 on piston 7, thereby facilitating the operation of the drill and elongating its life span.

Figure 3:
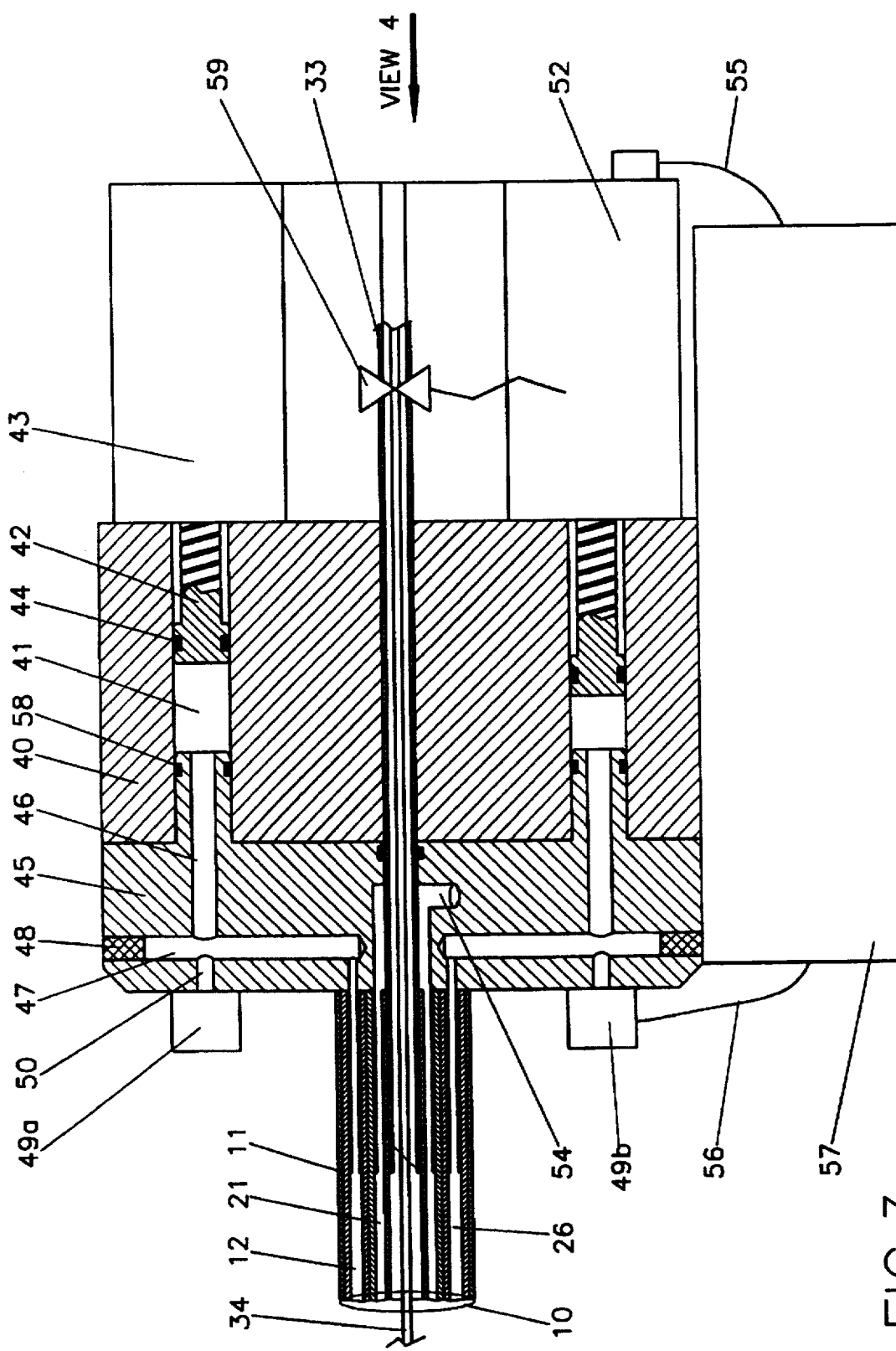
FIG. 3 is a view of longitudinal section of an illustrative embodiment of a driving unit according to the present invention.
Figure 4:
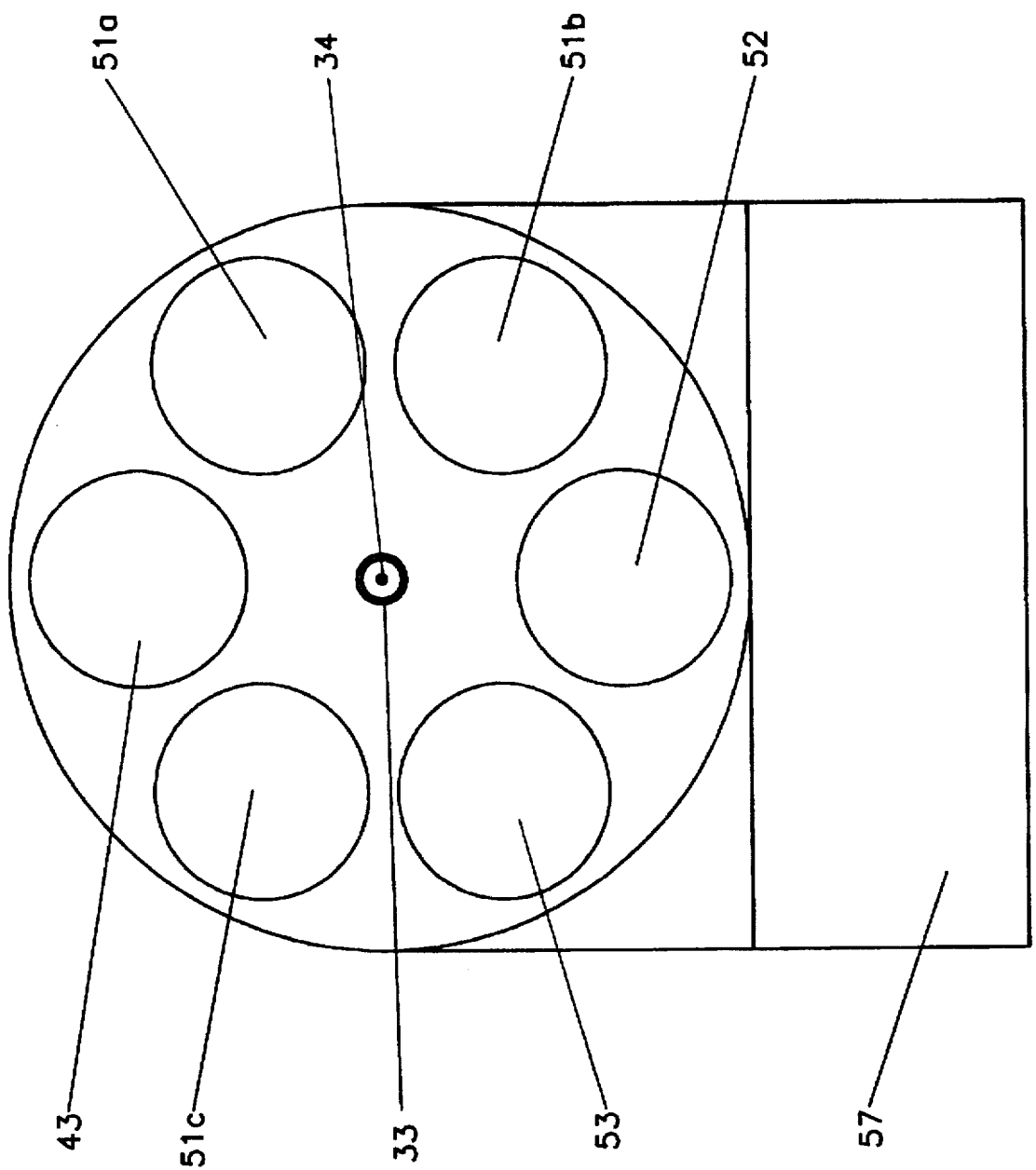
FIG. 4 is a view of the driving unit of FIG. 3 along view 4 in FIG. 3.

FIGS. 3 and 4 describe an embodiment of an illustrative driving unit such as might be used in a drill assembly according to the present invention. The role of driving unit, which is typically located at a convenient location outside the bore, is to supply pressure to the drill, to monitor the pressures, to direct the drill and to operate the various parts of the drill in proper sequence. The driving unit includes a housing 40 in which six bores 41 are circumferentially equally spaced. The following description relates to one channel which operates the working head 5 in linear and rotary movement, but it is applicable to all other channels.

Piston 42 is located inside bore 41. Piston 42 is attached to an electric linear actuator 43. Operation of linear actuator 43 increases or decreases the pressure in bore 41. Pressure is maintained with O-ring 44. Adapter 45 connects housing 40 to bundle 10. The pressure is maintained with O-ring 58. The pressure is transferred from bore 41 to lumen 12 through channel 46 and channel 47. It was previously described that the pressure in lumen 12 on the drill side, is used for pushing piston 7 forward. Plug 48 closes channel 47 and is used only for manufacturing purposes. A pressure sensor 49a is connected to lumen 47 via lumen 50, thus sensing the pressure in lumen 12.

FIG. 4 shows the arrangement of the linear actuators. Linear actuators 51a, 51b, 51c are used for pressurizing cylinder gripping balloons 2a, 2b, 2c, respectively. Linear actuator 52 operates piston 7 during the phase in which the drill advances forward. Linear actuator 53 operates working head gripping balloon 20 via channel 54.

The operation of the drill is controlled by electronic controller 57. The linear actuators, the pressure sensors and the positioning sensors are all connected to the controller 57. For example, linear actuator 52 is connected via electrical cable 55, pressure sensor 49b is connected via cable 56 and positioning sensors 4 located on the drill are connected with an electrical cable 39 (shown in FIG. 2). Some of the control functions of the controller are presented hereafter.

FIG. 1, demonstrates that when chamber 29 is pressurized, the pressure in chamber 15 should be decreased, and the pressure in chamber 32 should be kept constant, because chamber 32 is connected to working head gripping balloon 20.

Controller 57 can fulfill this assignment as it constantly monitors the pressures and can operate linear actuators 43, 52 and 53. Another function of controller 57 is to control the directional movement of the drill. Controller 57 receives data relating to the orientation of the drill from positioning sensors 4. By comparing the data and the desired direction it can command the linear actuators 51a, 51b, 51c to supply different pressures to cylinder gripping balloons 2a, 2b, 2c.

An additional function of controller 57 is to control the fluid jet used to remove the debris. Central tube 33 is located in the center of housing 40. Water jets are supplied to the drill through central tube 33. The flow through tube 33 can be controlled by a solenoid 59 which is operated by controller 57. All these functions, as well as others such as controlling the maximum pressure in the drill and connection to a host computer, can be carried out by controller 57.

It is to be understood that the drill described in this invention contains features that are not required for some applications. For example, in a pipe cleaner, the directional feature is not needed, because the drill is directed by the pipe. In this case the positioning sensors 4 are redundant and the three gripping balloons 2a, 2b, 2c can be connected to one lumen.

It is to be understood that the gripping balloons may be replaced by gripper shoes in a similar way as described in U.S. Pat. No. 4,314,615 to Sodder.

It is to be understood that in order to reduce the stresses on balls 18, two or more endless grooves 16, spaced longitudinally on piston 7 may be used.

It is to be understood that it is possible to operate the drill in such a way that for every forward movement of the drill the number of revolutions of the working head is arbitrary and should be decided according to the properties of the material to be removed.

While the invention has been described with respect to a limited number of embodiments, it will be appreciated that many variations, modifications and other application of the invention may be made.

What is claimed is:

1. A self-propelled drill assembly for drilling a bore having a wall, comprising:
   (a) a housing;
   (b) a piston slidable within said housing;
   (c) a working head connected to said piston;
   (d) a rotary piston driving mechanism for converting a longitudinal motion of said piston in said housing to a combined longitudinal and rotary movement of said working head;
   (e) a housing gripping device connected to said housing for gripping the drill to the wall of the bore to enable drilling; and
   (f) a working head gripping device connected to said working head for gripping said working head to the wall of the bore, to enable pulling the drill in a forward direction.

2. The drill assembly of claim 1, further comprising a driving unit for driving said rotary piston.

3. The drill assembly of claim 1, further comprising a bundle for connecting said rotary piston to said driving unit.

4. The drill assembly of claim 1, wherein said housing gripping device includes at least three circumferentially spaced gripping mechanisms.

5. The drill assembly of claim 4, wherein said gripping mechanisms are independently pressurized to different pressures, thereby enabling directing of the drill.

6. The drill assembly of claim 4, further comprising a positioning sensor to measure a position of the drill.

7. The drill assembly of claim 2, wherein said driving unit includes a pressure generator source, a controller for distributing the pressure in sequence to said piston, said housing gripping device, and said working head gripping device.

8. The drill assembly of claim 3, wherein said bundle includes a central tube.

9. The drill assembly of claim 1, wherein said rotary piston driving mechanism includes:
   (i) an endless guide groove defined in one of said piston and said housing and comprising a series of groove sections of generally alternating directions; and
   (ii) motion conversion means responsive to linear motion of said piston in said housing for causing said piston to rotate relative to said housing about said axis, said motion conversion means including at least one guide member secured in the other of said piston and said housing and projecting substantially radially and into said guide groove.

10. The drill assembly of claim 9, wherein said rotary piston driving mechanism further includes:
    (iii) directing means responsive to linear reciprocation of said piston for directing said guide member in a forward direction into circumferentially successive groove sections while preventing reverse directional movement of the guide member into a groove section that has been immediately previously traversed.

11. The drill assembly of claim 10, wherein each successive pair of said groove sections intersects at a respective apex, and wherein successive apices point in generally opposite longitudinal directions; and wherein said groove has first and second opposite side walls, wherein said guide member alternately bears forcefully against said first and second side walls in successive sections of said groove to define load bearing and non-load bearing side walls in each groove section, and wherein said directing means includes:

at each apex on the load bearing side wall, a smooth arcuate section positioned symmetrically with respect to the longitudinal axis of the piston for effecting smooth redirected movement of the guide member therealong into the next successive groove section in said forward section; and at each apex on the non-load bearing side wall, a discrete directional transition positioned asymmetrically with respect to the longitudinal axis of the piston so as to be passed by said guide member in said groove before said guide member is redirected into the next successive groove section by said symmetrical arcuate section.

12. The drill assembly of claim 9, wherein each successive pair of said groove sections intersects at a respective apex, and wherein successive apices point in generally opposite longitudinal directions; and wherein said directing means comprises a projecting member projecting into said groove adjacent each apex for forcing said guide member beyond said each apex only in said forward direction beyond said groove.

13. The drill assembly of claim 9, wherein each successive pair of said groove sections intersects at a respective apex, and wherein successive apices point in generally opposite longitudinal directions; and wherein said groove has first and second opposite side walls, wherein said guide member alternately bears forcefully against said first and second side walls in successive sections of said groove to define load bearing and non-load bearing side walls in each groove section, and wherein said directing means includes:

a plurality of recesses each defined in the load bearing surface adjacent the apex demarking the end of a respective groove section; and a plurality of gate members disposed in respective recesses, each gate member being resiliently biased to project out from said recess and into said groove, and configured to be forced into said recess in opposition to said resilient bias by said guide member traversing said groove in a forward direction and passing said recess, said gate member blocking movement of said guide member through said groove in a reverse directional movement.

14. A method of operating a drill to perform operation of boring, self-advancing and directing, the method comprising the steps of:

(a) providing a self-propelled drill for drilling a bore, said drill including:
 (i) a housing;
 (ii) a piston slidable within said housing;
 (iii) a working head connected to said piston;
 (iv) a rotary piston driving mechanism for converting a longitudinal motion of said piston in said housing to a combined longitudinal and rotary movement of said working head, said rotary piston driving mechanism including an endless guide groove defined in one of the piston and the housing and comprising a series of groove sections of generally alternating directions;
 (v) a housing gripping device connected to said housing for gripping the drill to the wall of the bore to enable drilling;
 (vi) a working head gripping device connected to said working head for gripping said working head to the wall of the bore, to enable pulling the drill in a forward direction; and
 (vii) a bundle for connecting the rotary piston to the driving unit;

(b) gripping the drill housing to the bore wall;

(c) operating the working head for drilling operation;

(d) gripping the working head;

(e) releasing the gripping of the housing;

(f) advancing the drill housing and the bundle attached to it one stroke of the endless groove; and (g) repeating steps (b) to (f).

15. The method of claim 14, further comprising removing the debris with fluid jets.

16. The method of claim 14, wherein said gripping the drill housing to the bore wall is effected asymmetrically for changing direction.

* * * * *